(12) United States Patent
Wenz et al.

(10) Patent No.: US 7,018,089 B2
(45) Date of Patent: Mar. 28, 2006

(54) APPARATUS AND METHODS FOR MIXING TWO COMPONENTS

(75) Inventors: Robert Wenz, Wollstadt (DE); Paul M. Sand, San Carlos, CA (US)

(73) Assignee: Kyphon Inc., Sunnyvale, CA (US)

( * ) Notice: Subject to any disclaimer, the term of this patent is extended or adjusted under 35 U.S.C. 154(b) by 177 days.

(21) Appl. No.: 10/660,465

(22) Filed: Sep. 10, 2003

(65) Prior Publication Data

US 2004/0122359 A1    Jun. 24, 2004

(30) Foreign Application Priority Data

Sep. 17, 2002 (DE) ................................ 102 42 984

(51) Int. Cl.
*B01F 13/00* (2006.01)
(52) U.S. Cl. ................ 366/130; 366/256; 366/332; 604/89; 222/246; 206/219; 206/221
(58) Field of Classification Search ............ 604/82–92; 206/219, 221; 222/246; 366/129, 130, 256, 366/257, 268, 269, 332, 337
See application file for complete search history.

(56) References Cited

U.S. PATENT DOCUMENTS

| | | | |
|---|---|---|---|
| 2,869,543 A * | 1/1959 | Ratcliff et al. ................. 604/90 |
| 3,144,966 A | 8/1964 | Cook |
| 3,437,242 A | 4/1969 | Poitras |
| 3,477,431 A * | 11/1969 | Walecka ...................... 604/89 |
| 3,684,136 A | 8/1972 | Baumann |
| 3,739,947 A | 6/1973 | Baumann et al. |
| 3,756,571 A | 9/1973 | Winberg |
| 3,828,434 A | 8/1974 | Mosch |
| 3,831,742 A | 8/1974 | Gardella et al. |
| 3,881,484 A * | 5/1975 | Gidcumb, Jr. ............... 604/89 |
| 3,917,062 A | 11/1975 | Winters |
| 4,084,320 A | 4/1978 | Skeirik |
| 4,116,240 A * | 9/1978 | Guiney ........................ 604/89 |
| 4,551,135 A | 11/1985 | Gorman et al. |
| 4,826,047 A | 5/1989 | Heflin |
| 5,058,770 A | 10/1991 | Herold et al. |
| 5,429,603 A | 7/1995 | Morris |
| 5,630,800 A * | 5/1997 | Blank et al. .................. 604/82 |

(Continued)

FOREIGN PATENT DOCUMENTS

DE       34 39 975 A       6/1985

(Continued)

*Primary Examiner*—David Sorkin
(74) *Attorney, Agent, or Firm*—Townsend and Townsend and Crew LLP

(57) ABSTRACT

The apparatus for production of mixtures from two components has a container for each and devices to combine the components in the mixing space and for extrusion of the mixture. The powdered component (4) is situated in the lower part of the inner space (21), which is sealed by a bottom (10). This carries a nozzle (2) with closure membrane (3). The inner space (21) is closed on the top by the lower wall (6) and the sliding seal (8). The liquid component (9) is situated in the inner space (18) of the inner hollow cylinder (5). This is closed on the top by the upper wall (11). The lower and upper wall (6) and (11) each have an opening with sealing lips (7) and (12) that are closed by parts of the mixing rod (15). A torus (20), a section with smaller diameter (19), a mixing disk (22), as well as a mandrel (24), are present on the lower part of the mixing rod (15).

17 Claims, 5 Drawing Sheets

U.S. PATENT DOCUMENTS 6,544,233 B1 * 4/2003 Fukui et al. ................ 604/191
6,626,912 B1    9/2003 Speitling

FOREIGN PATENT DOCUMENTS

| | | | |
|---|---|---|---|
| EP | 0 188 981 A | 7/1986 |
| EP | 0 245 788 A1 | 11/1987 |
| EP | 0 380 867 A1 | 8/1990 |
| EP | 0 397 589 A1 | 11/1990 |
| GB | 2239818 A | 7/1991 |

* cited by examiner

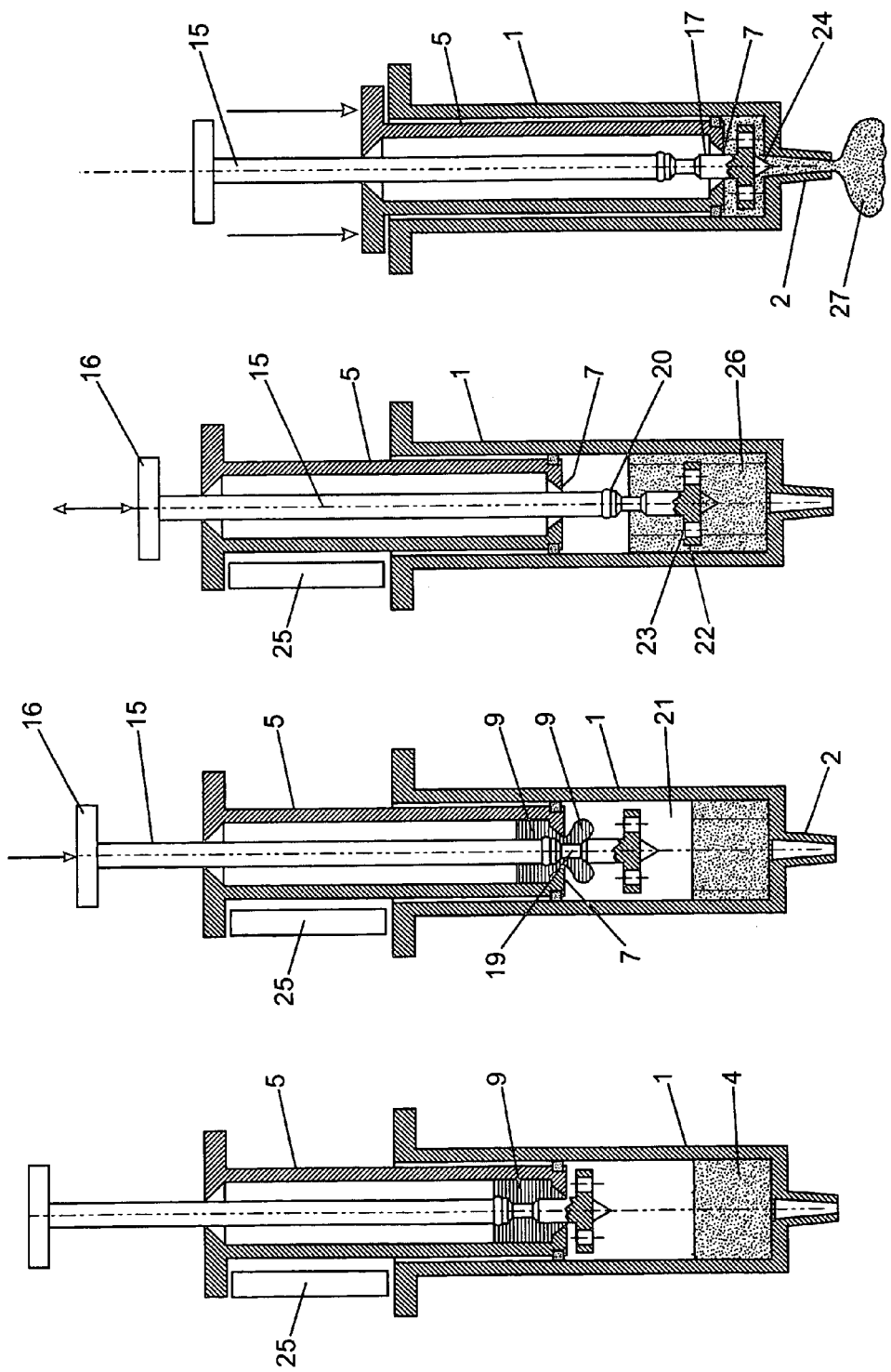

APPARATUS AND METHODS FOR MIXING TWO COMPONENTS

CROSS-REFERENCES TO RELATED APPLICATIONS

This application claims priority from German Patent Application No. 102 42 984.7, filed on Sep. 17, 2002, the full disclosure of which is incorporated herein by reference.

BACKGROUND OF THE INVENTION

1. Field of the Invention

The present invention relates generally to medical apparatus and methods and more particularly to devices and methods for mixing components prior to delivery of the mixed components to an anatomical site.

It is frequently desirable or necessary to mix components of a medical preparation together immediately prior to use. It is also desirable to mix components in single use batches, to assure consistency in the delivery of the combined components. Compositions such as bone fillers, bone cements, medical adhesives, dental adhesives, and the like, often rely on mixing syringes combining components and subsequently delivering the combined components to the desired anatomical location. Frequently, the mixing syringes or other apparatus are also used for storing and maintaining sterility of the components for extended periods prior to the time when they are to be used.

To be successful, such storage and mixing apparatus should meet a number of objectives. First, the apparatus must store the separate components in a manner that provides complete isolation prior to mixing. Once it is desired to mix the components, however, mixing must be rapid, thorough, and require minimum effort by the user. Many prior art devices rely on shaking or vibrating the mixing syringe or other container to achieve adequate mixing of the components. Shaking or vibration, however, seldom achieves complete mixing and can compromise the design of the syringe. Moreover, such devices frequently require external mixing systems which can be expensive and inconvenient to use.

For these reasons, it would be desirable to provide improved mixing syringes and other apparatus for combining and mixing components of medical and dental compositions prior to use in single use batches. It would be further desirable if such mixing syringes and apparatus were also useful for directly or indirectly delivering the combined and mixed materials to the anatomical site of interest. Such mixing syringes and apparatus should be relatively inexpensive to produce, should provide complete and reliable isolation of the components to be mixed prior to use, should be suitable for both liquid-powder and liquid-liquid mixes, should be relatively simple to use, and should provide precise and accurate delivery of the mixed compositions. At least some of these objectives will be met by the inventions described herein below.

2. Description of Background Art

U.S. Pat. No. 3,739,947 and U.S. Pat. No. 3,684,136 describe a syringe (comparable to an injection syringe without needle) that contains a sealed liquid reservoir for first component on one end. The space to accommodate the second component is hermetically separated from this liquid reservoir. To produce the mixture, the seal is perforated so that separation of the two components is eliminated (the syringe is activated).

GB 2239818 describes mixing apparatus that contains no integrated mechanical mixing device. After combining of the two components, this apparatus must be shaken for mixing. There is a hazard that a homogeneous mixture will not be produced, especially since it is difficult to mix viscous material systems by shaking. The two containers to accommodate the two components are sealed relative to each other by means of a membrane which is difficult and costly to fabricate.

U.S. Pat. No. 4,551,135 describes a mixing device for extrusion of two different components where the device includes two vessels which must be separated for storage of the two components before extrusion.

U.S. Pat. No. 3,756,571 describes an apparatus that requires an expensive, external shaking or mixing device for homogeneous mixing of two components. The container to accommodate the liquid component is not suitable for extrusion of the finished mixture. A seal (film) provides separation of the two components (powder and liquid) in the two vessels.

U.S. Pat. No. 3,828,434 describes a mixing capsule in which homogeneous mixing of two components is provided by an external shaking device.

EP 0 245 788 A1 describes an apparatus including two containers to accommodate the two components. The containers are hermetically sealed from each other, and the apparatus requires an external mixing device.

EP 0 397 589 A1 describes an apparatus where a first component (liquid) is conveyed by means of a pressure difference between a first container holding the liquid to a second container holding a second component (powder). The container for the liquid is sealed relative to the other containers.

U.S. Pat. No. 3,831,742, U.S. Pat. No. 3,917,062 and U.S. Pat. No. 4,084,320 describe an apparatus which requires an external mixing device.

EP 0 380 867 A1 describes an apparatus intended for mixing of bone cements using partial vacuum. One container must be coupled to another container. The two containers are therefore not integrated in a common enclosure.

U.S. Pat. No. 5,058,770 describes an apparatus with two containers that contain the two components to be mixed. The containers must be screwed together first before the mixing process. The vessel containing the liquid is closed by a membrane that must be perforated for mixing of the two components.

BRIEF SUMMARY OF THE INVENTION

The present invention in its various aspects and embodiments, as described in detail below, can provide the following improvements and benefits over prior mixing syringes and systems, either individually or in combination. For example, the mixing syringes and apparatus of the present invention can provide for the complete separation of two components in a device which is suitable for both storage and for subsequent delivery of the combined components. In a preferred design, a mixing syringe according to the present invention allows for simple release of a liquid component into a powder or other second component by gravity upon opening of a flow path within the apparatus. The invention can further provide for on-board mixing of the combined components using an integral mixing implement in the apparatus. In a particularly preferred design, the mixing implement also forms part of the release mechanism which opens a flow path for the liquid. The mixing syringes and apparatus can also provide for the precisely metered delivery of the combined and mixed components, preferably using a piston which in the exemplary embodiments is used to hold the liquid component prior to combination.

In a first aspect of the present invention, a mixing syringe or other delivery apparatus comprises a syringe barrel, a plunger, and a mixing rod. The syringe barrel has a hollow interior and an outlet nozzle at its lower end. The hollow interior will be suitable for holding the second component to be mixed, typically a powder. The powder may consist of bone filler materials such as autograft or allograft bone graft tissue, granulated bone material harvested from coral, demineralized bone matrix, calcium phosphate compositions or poly(methyl methacrylate) cement. The plunger also has a hollow interior and is reciprocatably disposed in the hollow interior of the syringe barrel. The hollow interior of the plunger is suitable for holding the liquid component prior to mixture with the powder or other second component. The liquid component may consist of a buffered aqueous solution, glycerol or methyl methacrylate monomer. The mixing rod is also reciprocatably disposed in the hollow interior of the syringe barrel and has a mixing element at its lower end. The mixing element is adapted to mix the combined liquid component and second component in the hollow interior of the syringe barrel upon reciprocation of the mixing rod, either axial reciprocation, rotational reciprocation, or both.

As a particular advantage of the present invention, the plunger and the mixing rod are adapted to have a first relative position where the hollow interiors of the syringe barrel and the plunger are sealed from each other. Thus, the liquid and second component to be mixed may be held and stored for prolonged periods of days, weeks, months, or longer in the mixing syringe while the plunger and mixing rod remain in their first relative position. The liquid may be released into the hollow interior of the mixing syringe, however, by moving the plunger and the mixing rod to a second relative position where the hollow interiors are in fluid communication. In the exemplary embodiments, the mixing rod will be advanced axially relative to a bottom wall of the plunger, opening a flow path between their respective hollow interiors. It will be appreciated, however, that such a flow path could be opened in a number of other ways, including relative rotation of the mixing rod and the plunger, e.g., to align holes or other passages in the mixing rod assembly with holes or passages in the bottom wall of the plunger.

Optionally, the mixing syringe further includes a sealing cylinder that may be inserted into the hollow interior of the plunger to cover, isolate, and seal the liquid component which has been introduced to the hollow interior. Usually, the sealing cylinder will include at least one sliding seal, typically an O-ring, near its bottom and to provide a hermetic seal over the liquid-filled chamber which is created in the lower end of the plunger interior. Further preferably, the sealing cylinder and plunger will have a locking mechanism to hold the cylinder in place within the plunger after it has been inserted to a desired position.

In a second aspect of the present invention, a method for mixing a liquid component and a second component comprises providing the second component, which may be a liquid, solid, but will usually be a powder, at the bottom of a hollow interior of a syringe barrel. A liquid component is provided at the bottom of a hollow interior of a plunger. The liquid is released from the plunger to combine with the second component in the syringe barrel by moving a mixing rod relative to the plunger. The mixing rod is then reciprocated, either axially, rotationally, or both, to mix the liquid component and the second component together. Usually, after adequate mixing, the plunger is advanced to extrude the mixed component from the syringe barrel through a nozzle or other outlet to a desired target site. In a particularly preferred example, the liquid component and second component are combined to form a bone cement or filler, and the mixed composition is delivered to a target bone, such as the interior of a vertebral body.

The liquid component can be released from the interior of the plunger to the interior of the syringe body to combine with the second component in a variety of ways. In the exemplary embodiments, the mixing rod has a first position relative to the plunger where the mixing rod blocks or closes a flow path between the hollow interior of the plunger and the hollow interior of the syringe barrel. By moving the mixing rod, either axially, rotationally, or some combination thereof, the flow path becomes unblocked to allow liquid flow, typically by gravity. In a particular embodiment, the mixing rod has an annular depression which aligns with a passage in a bottom wall of the plunger to open the liquid flow path. In other embodiments, the passage may be closed by sliding seals, such as O-rings, where displacement of the sliding seals from the passage permits sufficient space for the liquid to flow into the syringe barrel.

BRIEF DESCRIPTION OF THE DRAWINGS

FIGS. 2–5 illustrate use of the mixing syringe of FIG. 1 for combining and mixing a liquid component and powder component and subsequently delivering the combined and mixed components to a target site.

DETAILED DESCRIPTION OF THE INVENTION

Figure 1:
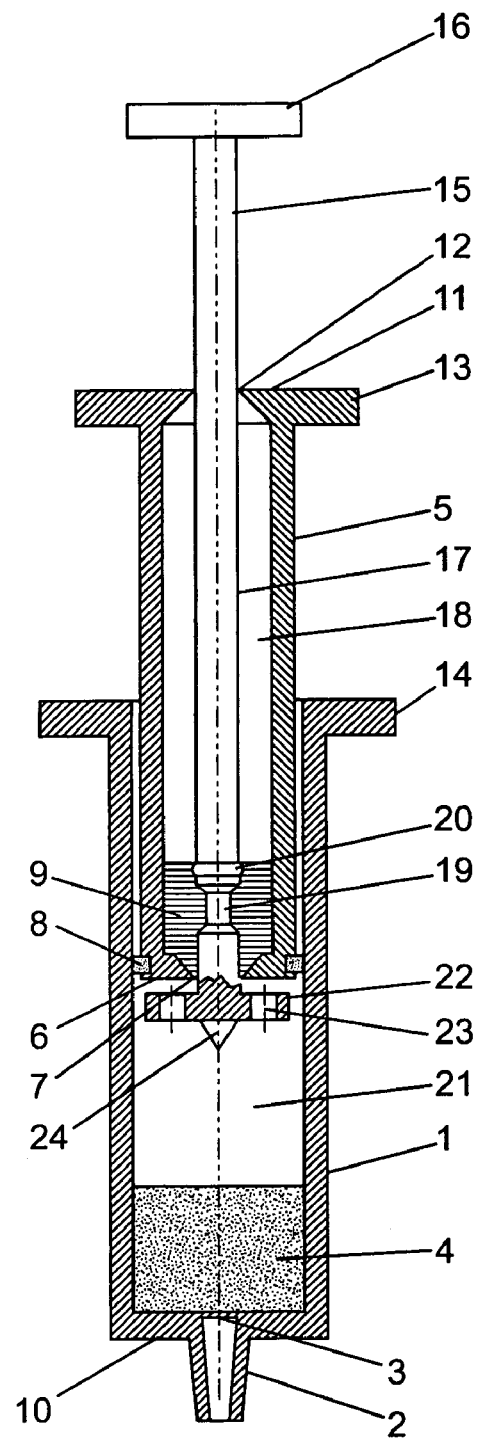
FIG. 1 is a cross-sectional view of a first embodiment of a mixing syringe constructed in accordance with principles of the present invention.

The apparatus according to the invention consists of three main components. Additional components that are explained later belong to the embodiment of the invention. An outer hollow cylinder, closed on its lower end includes a bottom provided with a nozzle from which the finished mixture emerges during extrusion. Between an internal space or volume of the nozzle and the hollow cylinder, a closure membrane is found that is perforated right before extrusion. Alternatively, the nozzle may be closed relative to the closure membrane with a stopper.

The outer hollow cylinder serves as vessel for holding the powdered component of the material system (powder container), which is situated in its lower region or volume. This lower region of the outer hollow cylinder also serves as mixing space. The mixing space may have a volume of approximately 70 ml. Of course, other size mixing spaces could be used depending upon the volume of the materials to be mixed and the size of the mixing rod and disk and related components. The volume of powdered component may range from approximately 10 ml to 60 ml, with an exemplary volume of approximately 30 ml. The volume of the liquid component may range from approximately 5 ml to 30 ml, with an exemplary volume of approximately 15 ml. On its upper end, the outer hollow cylinder includes an annular flange that facilitates operation, for example, during the extrusion process.

An inner hollow cylinder is closed on its lower end with a lower wall and on its upper end with an upper wall. An annular flange is also provided as part of the upper wall and facilitates extrusion. The space enclosed between the two walls is the liquid container and serves to accommodate the liquid component.

This inner hollow cylinder is inserted into the upper part of the outer hollow cylinder and has an outside diameter that is only slightly smaller than the inside diameter of the outer hollow cylinder. A sliding seal is situated on the outer periphery of the inner hollow cylinder. This is arranged in the region of its lower end in the vicinity of the lower wall and is sealed against the inner wall of the outer hollow cylinder. The inner hollow cylinder with its sliding seal therefore acts as a plunger or piston in the outer hollow cylinder and is used for extrusion of the finished mixture. As described hereinbelow, the outer hollow cylinder is sometimes referred to as a syringe body and the inner hollow cylinder as a plunger.

The powder container or volume in the interior of the outer hollow cylinder is bordered on its upper side by the lower wall of the inner hollow cylinder or plunger. The lower wall has a central opening that has a sealing lip and, together with the lower end of a mixing rod (described below), forms a valve. This valve can be opened downward by axial displacement of the mixing rod. This closes the central opening in the raised position, whereas it exposes an annular gap in the lowered position, since a section of the mixing rod is then situated in the region of the central opening, which has a smaller diameter than it.

The upper wall of the inner hollow cylinder also has a central passage or opening with a sealing lip through which the mixing rod is passed so that the rod can be axially reciprocated and/or rotated about its axis. The rod is sealed against the sealing lip, so that no liquid can emerge.

The mixing rod has a larger diameter in its upper and lower regions which are dimensioned so that they seal against the sealing lips of the upper and lower wall of the inner hollow cylinder. Between the larger diameter regions, the mixing rod has a significantly smaller diameter over a short length. Thus, axial adjustment of the mixing rod to align its small diameter region within the opening or passage in the lower wall of the inner cylinder or plunger opens a flow path for the liquid thus acting as a valve to release the liquid component into the powder component.

In the region of the mixing rod just above the smaller diameter region, a torus is situated on the larger diameter region, dimensioned so that it can be pushed through the sealing lip. The user feels a distinct resistance which indicates that the mixing rod has been readied for mixing, as will now be described.

The mixing rod has a mixing disk on its lower end. The mixing rod is dimensioned so that the layered components can be mixed homogeneously with each other after opening of the valve. To improve the mixing result, the mixing disk is provided with perforations and optionally nubs, bumps, or other surface features. The mixing rod is axially reciprocated and/or rotationally oscillated to provide mixing. On its lower end, the mixing rod is equipped with a flange plate that serves as an operating element and facilitates operation, for example, during the mixing process.

Methods according to the present invention will now be described. The following discussion is directed specifically at combining and mixing a "liquid component" with a "powdered component". The apparatus and methods according to the invention, however, are useful for combining a liquid component stored in the inner cylinder/plunger with any other type of component(s) stored in the mixing volume, including liquid components, viscous components, pasty components, solid components, etc.

The outer and inner hollow cylinders are separated from each other by pulling apart, and a pre-selected amount of the powdered component is filled into the lower region of the outer hollow cylinder (syringe body). The inner hollow cylinder (plunger) is then rotated upward, and the mixing rod is pushed until the valve is opened. The liquid component is then filled into the inner hollow cylinder through the open valve, eliminating the need for a costly seal. After closure of the valve, the inner hollow cylinder (plunger) is inserted into the outer hollow cylinder (syringe body) up to a mark to leave a mixing space of a predetermined volume. The apparatus is ready for operation but will usually be sealed into an airtight plastic enclosure or other suitable package for transport and storage. The package is preferably sterilized, typically with ionizing radiation.

The user opens the package and removes the apparatus according to the invention. The user holds it with the nozzle downward and pushes the mixing rod until the valve is opened. This is noticeable in that the mixing rod can be moved more easily with the valve opened. Visual confirmation of opening is usually also possible, since the outer hollow cylinder is preferably made from a transparent plastic, such as a polycarbonate, polypropylene, polyethylene, polyurethane, polyolefin, nylon or other suitable material.

When the liquid component has flowed completely from the liquid container into the powder container filled with the powdered component, the mixing rod is reciprocated back and forth in oscillating fashion for mixing. Backflow of the mixture into the liquid container, in which the liquid component was previously found, is not possible, since the valve is closed again, since the large diameter upper region of the mixing rod when it is situated in the passage in the lower well of the inner cylinder when the mixing rod is in the mixing position. In order for the valve not to be inadvertently opened during the mixing process, the mentioned torus is present. This forms a distinct resistance during displacement of the mixing rod when it strikes against the sealing lips, so that the user realizes that he must reverse the movement. This design thus avoids the need for a costly external mixing device.

After homogeneous mixing of the two components, the mixing rod is fully lowered and, by vigorous final pushing, the closure membrane is perforated with the tip of the mixing rod. The mixing rod is then pulled upward to the stop. The torus then passes the sealing lip and the valve is briefly opened and then closed again.

The apparatus according to the invention is then held vertically with the nozzle pointed downward and is ready for extrusion of the finished mixture. For extrusion, the inner hollow cylinder (plunger), is pushed downwardly into the outer cylinder (syringe body). The mixture emerges through the perforated membrane and nozzle. The design is simplified and the cost reduced because of the dual function of the inner hollow cylinder for both liquid containment and as a plunger.

The apparatus according to the invention will usually be used manually, and optionally may employ a powered or hand-operated press, with which the inner hollow cylinder (plunger) is mechanically advanced into the outer hollow cylinder. Such presses are known in construction for forcing out viscous construction materials and are not an object of the present invention.

The apparatus according to the invention is explained below by means of examples and a total of 8 figures, having the following content.

Referring now to FIG. 1, the outer hollow cylinder 1 is closed on its lower end with a bottom 10 that is connected to a nozzle 2 that is closed by means of a closure membrane 3 relative to the internal space of the outer hollow cylinder 1. The powdered component 4 is situated in the lower region of the outer hollow cylinder 1.

The powder container for storage of the powdered component 4 is formed by the inner space 21 of the outer hollow cylinder 1, which is bounded by the cylinder wall and the bottom 10 in the lower region and the inner hollow cylinder 5 acting as piston in the upper region.

An annular flange 14, whose outside diameter is much greater than the outside diameter of the outer hollow cylinder 1, is arranged on the upper end of the outer hollow cylinder 1. This annular flange 14 facilitates handling of the apparatus according to the invention, especially during extrusion of the finished mixture.

The inner hollow cylinder 5 is arrange axially displaceable in the upper region of the outer hollow cylinder 1, which is sealed on its lower end from the lower wall 6, which is provided in its center with an opening having a sealing lip 7. Since the inner hollow cylinder 5 during extrusion of the finished mixture assumes the function of a piston, it is sealed relative to the inner wall of the outer hollow cylinder 1 by means of a sliding seal 8. The liquid component 9 is stored in the lower region of the inner hollow cylinder 5.

In its upper region, the inner hollow cylinder 5 is bounded by an upper wall 11 that has an opening with a sealing lip 12 in its center. The upper wall 11 is connected to an annular flange 13, whose outside diameter is much greater than the outside diameter of the inner hollow cylinder 5.

The liquid container for storage of the liquid components 9 is formed by an inner space 18 of inner hollow cylinder 5, bounded by the cylinder wall, as well as the lower wall 6 and the upper wall 11.

A mixing rod 15 is arranged concentrically in the inner space of inner hollow cylinder 5, which is equipped on its upper end with a flange plate 16 that serves as operating element. The mixing process is therefore facilitated for the operator. The larger diameter 17 of the mixing rod 15 is dimensioned both in the upper and lower region, so that the mixing rod 15, in cooperation with the two sealing lips 7 and 12, guarantees reliable sealing of the inner space 18. The mixing rod 15 has a smaller diameter 19 in a partial region in the lower region.

The lower part of the mixing rod 15 with the larger diameter 17 and the smaller diameter 19, together with the sealing lip 7, forms a valve that can be opened and closed by axial displacement of the mixing rod 15. The valve is closed when the mixing rod 15 is pushed fully upward and its partial region is sealed against sealing lip 7 with the larger diameter. It is opened when the mixing rod 15 is pushed somewhat downward, and its partial region with the smaller diameter 19 is situated in the region of sealing lip 7.

Above the region with the smaller diameter 19, the mixing rod 15 has a torus 20, whose outside diameter is dimensioned so that it can be pushed through the sealing lip 7, but a distinct resistance is then noticeable.

On its lower end, the mixing rod is connected to a mixing disk 22, having openings 23 that serve to achieve better mixing effect. A mandrel 24 is situated beneath the mixing disk 22, which serves to perforate the closure membrane 3 when the mixing process is ended and the mixture is to be extruded.

Operation of the device of FIG. 1 will be described with reference to FIGS. 2–5. FIG. 2 shows the apparatus in the storage transport state, filled with the powdered component 4 and the liquid component 9. In order to prevent undesired displacement of the internal hollow cylinder 5 relative to the outer hollow cylinder 1, a removable spacer 25 is arranged between the annular flanges 13 and 14.

FIG. 3 shows the apparatus according to the invention with the opened valve in the vertical position and with the nozzle 2 downward. For opening of the valve, mixing rod 15 is pushed downward by pressing on its flange plate 16 until its partial region with the smaller diameter 19 is situated in the region of sealing lip 7. The spacer 25 then prevents the inner hollow cylinder 5 from being pushed in undesired fashion. The liquid component 9 can now flow by gravity into the inner space 21 of the outer hollow cylinder 1.

FIG. 4 shows the apparatus during the mixing process. By further pressing on flange plate 16 of mixing rod 15, this is initially pushed further downward, in which case the torus 20 has passed the sealing lip 7. The valve between the inner space 18 of the inner hollow cylinder 5 and the inner space 21 of the outer hollow cylinder 1 is closed again, since the partial section with the larger diameter 17 is again situated in the region of sealing lip 7. The closed valve prevents part of the mixture from flowing in undesired fashion from the inner space 21 serving as mixing space into the empty inner space 18.

By further final pushing, the mixing rod 22 is finally pushed into the material 26. By oscillating back and forth movement of mixing rod 15, homogeneous mixing of the two components then occurs. During the mixing process, this is forced through the openings 23. The mixing process is accelerated by the turbulences and eddies that are then formed. Undesired displacement of the inner hollow cylinder 5 relative to the outer hollow cylinder 1 is also avoided during the mixing process by the spacer 25.

FIG. 5 shows the apparatus during extrusion of the finished mixture from the two components. To initiate this process, the mixing rod 15 is initially pushed fully downward until its mandrel 24 reaches the closure membrane 3 and perforates it by final pushing. The mixing rod 15 is then pulled upward to the stop, in which its partial region with the larger diameter 17 is again situated in the region of the sealing lip 7. The valve between the inner hollow cylinder 5 and the outer hollow cylinder 1 is therefore closed again. This prevents the finished mixture from flowing in undesired fashion from the inner space 21 into the inner space 18 during extrusion.

After removal of the spacer 25, extrusion can be carried out by pressing on the annular flange 13 of the inner hollow cylinder 5. The inner hollow cylinder 5 with its lower wall 6 and sliding seal 8 then assumes the function of a piston. For more convenient handling, the user can support his fingers on the annular flange 14 of the outer hollow cylinder 1. To the extent that the inner hollow cylinder 5 is pushed downward, the finished mixture 27 emerges from the nozzle 2.

Figure 6:
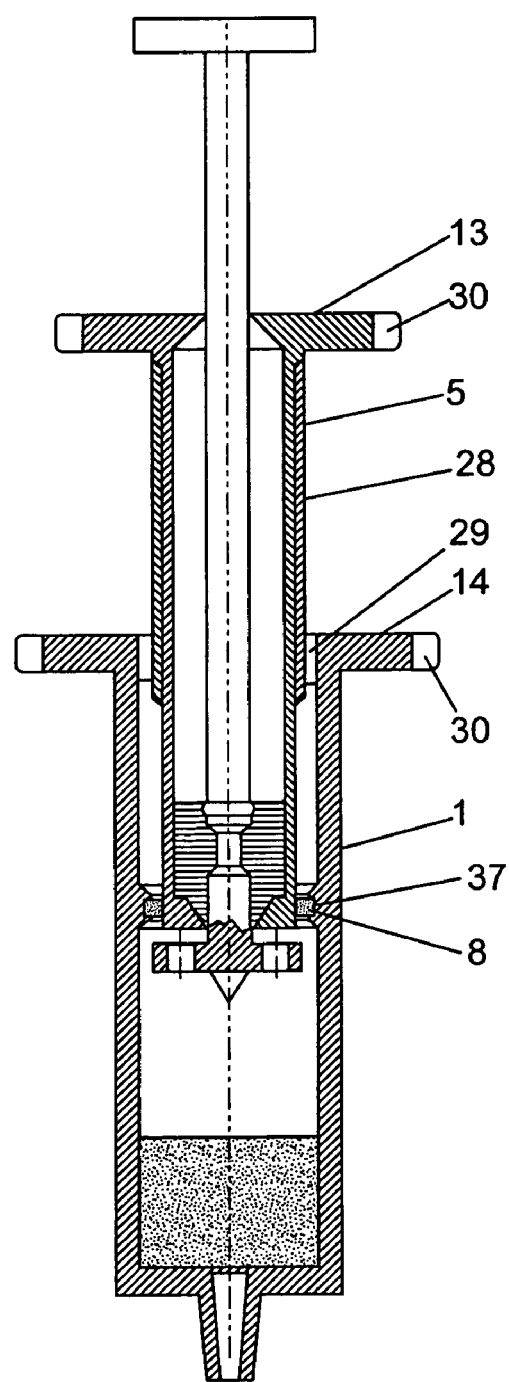
FIG. 6 is a second embodiment of a mixing syringe similar to the first embodiment but further including a threaded engagement between a plunger and syringe barrel for the controlled delivery of the combined substance after mixing.

FIG. 6 shows the apparatus according to the invention in a variant that has a thread between the outer periphery of the inner hollow cylinder 5 and the inner periphery of the outer hollow cylinder 1. For this purpose, the inner hollow cylinder 5 is provided with an outside thread 28 and the outer hollow cylinder 1 with an inside thread 29. This thread facilitates finely metered extrusion significantly, since, by rotating the inner hollow cylinder 5 relative to the outer hollow cylinder 1, very fine advance movements (stroke movements) can be executed. To increase handling capability, a knurling 30 is present both on the annular flange 13 and on annular flange 14. The sliding seal 8, which, in this variant, is inserted into an annular groove 37 on the inside periphery of the outer hollow cylinder 1, ensures sealing.

Figure 7:
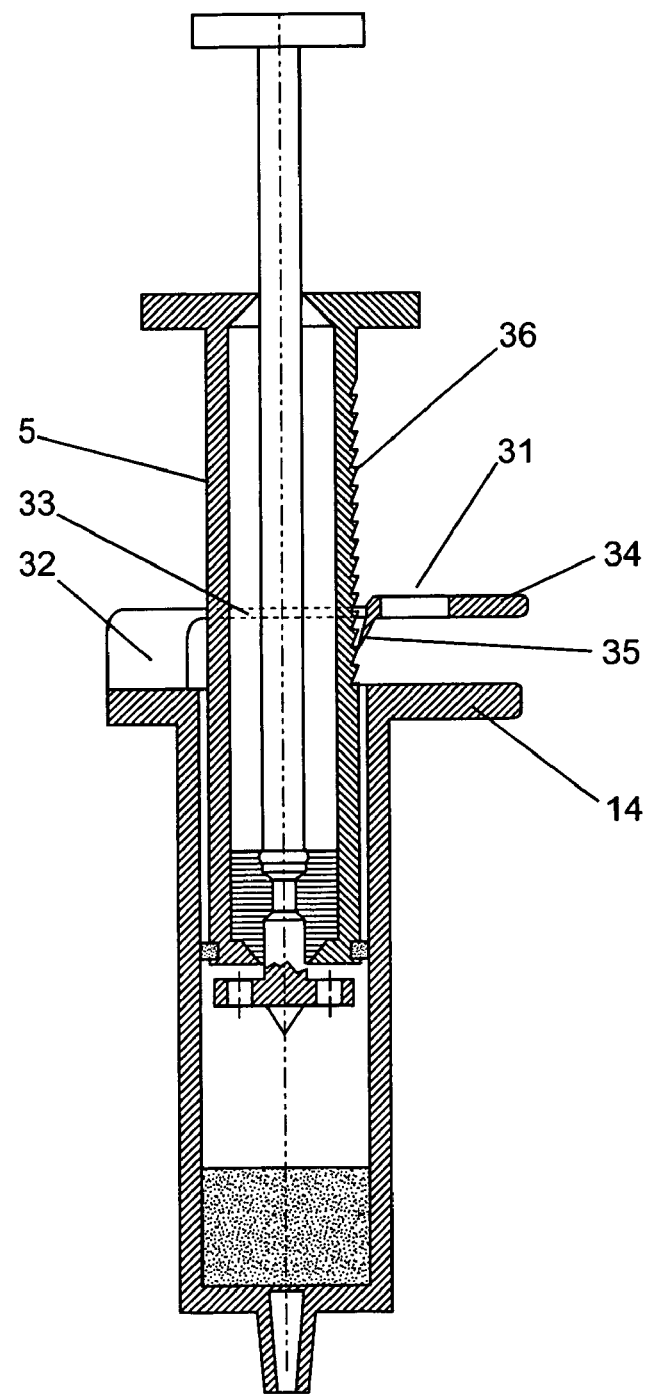
FIG. 7 illustrates a third embodiment of the apparatus of the present invention having a ratchet mechanism for advancing a plunger relative to the syringe barrel.

FIG. 7 shows the apparatus according to the invention in a variant equipped with a ratchet-advance device. This device also serves to facilitate finely metered extrusion.

The ratchet advance device is attached with its operating part 31 on the annular flange 14 of the outer hollow cylinder 1. This is designed as follows: the connection part 32 is connected on the left side of the annular flange 14 firmly to it and carries two spring elements 33. One of the two spring elements 33 cannot be seen in FIG. 7, since it is arranged symmetric to the plane of the drawing and therefore lies in front of the plane of the drawing in the sectional view. The two spring elements 33 are connected on the right side to each other with an operating element 34. This carries on its bottom a detent 35 that engages into toothing 36 on the right outside of the inner hollow cylinder 5, when the operating element 34 is pushed downward.

For extrusion, the user presses on the operating element 34, in which case he supports his hand on the annular flange 14. The spring element 33 is bent downward by the force exerting in this case, so that the operating element 34 with the detent 35 is also moved downward. The detent 35 is moved on a circular trajectory with an axial and a radial movement component (the latter in the direction of the longitudinal axis of the apparatus).

By this radial movement component, the detent 35 engages in the toothing 36 and moves this a bit in the axial direction. The detent 35 is designed so that it takes up the radial movement component by elastic bending. After release of the operating element 34, the spring element 33 assumes its original position again and the next advance movement can be initiated by pressing on the operating element 34. Finely metered extrusion of the finished mixture is therefore possible with particular convenience.

Figure 8:
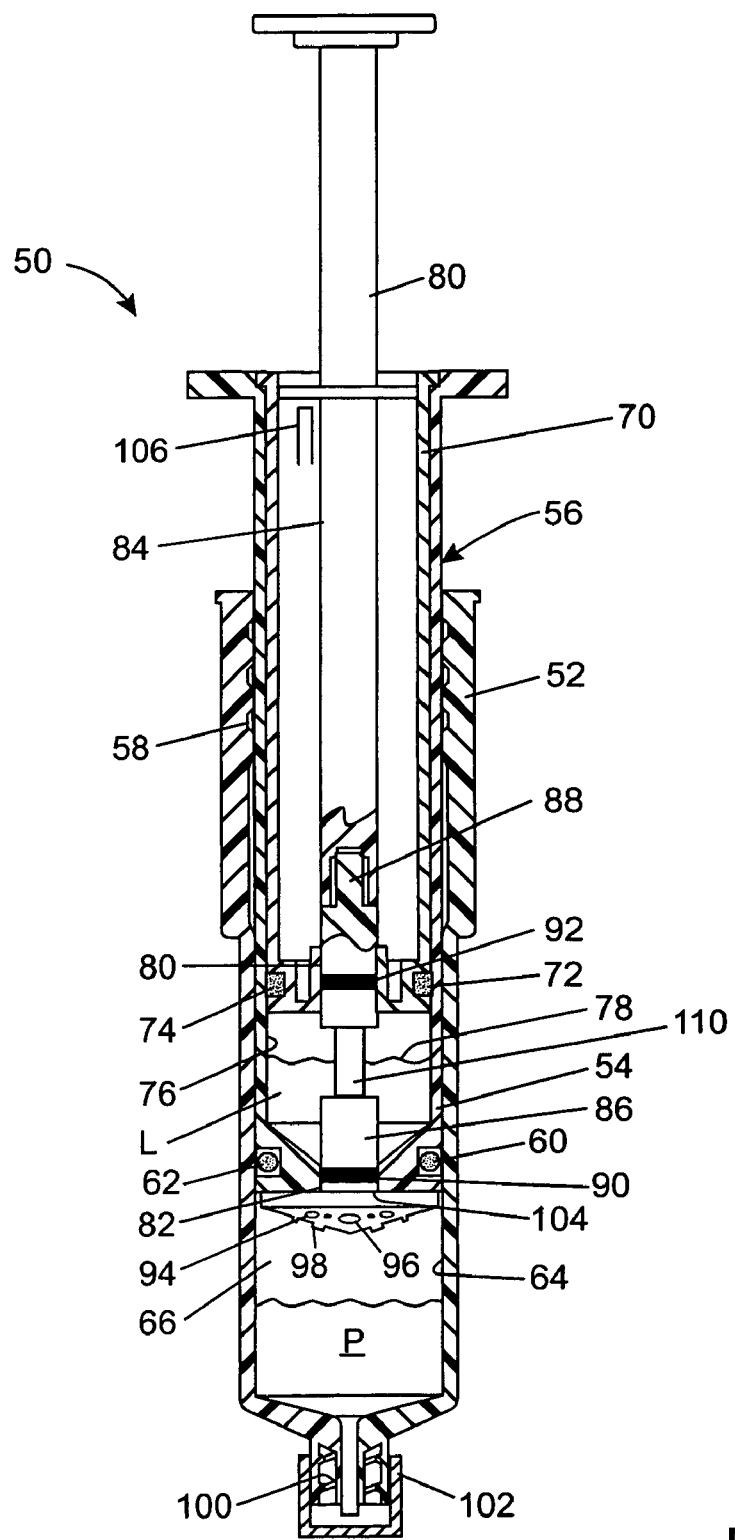
FIG. 8 illustrates a fourth embodiment of the apparatus of the present invention having a seal mechanism for containing a liquid component in the plunger prior to release into the syringe body.

A fourth embodiment of a mixing syringe 50 constructed in accordance with the principles of the present invention is illustrated in FIG. 8. The mixing syringe 50 comprises a syringe body or barrel 52 in the form of a hollow cylinder, a plunger 54, also in the form of a hollow cylinder, having threads 56 formed over an upper portion thereof. The threads 56 engage mating threads 58 within an upper portion of the syringe body in a manner similar to that described in connection with the embodiment of FIG. 6 above. Preferably, the threads have a multi-start configuration that will advance the plunger more rapidly than a single lead thread. A sliding seal in the form of an O-ring 60 is received in a slot 62 formed at the lower end of the plunger 54. The seal 60 engages an inner surface 64 of the hollow interior of the syringe body 52 to seal a mixing volume 66 at its lower end which contains a powder P or other second substance to be mixed.

A sealing cylinder 70 is slidingly received in the hollow interior of the plunger 54. A sliding seal 72 typically in the form of an O-ring is received in a slot 74 at the lower end of the sealing cylinder 70 to seal against the interior surface 76 of the sealing cylinder. Thus, a sealed volume 78 which holds the liquid L to be mixed is formed at the bottom of the interior of the plunger 54.

A mixing rod 80 is slidably received in the interiors of the syringe body 52 and the plunger 54, and passes through a first opening or passage 80 in the bottom of the sealing cylinder 70 and a second passage 82 in the bottom of the plunger 54. The mixing rod 80 is formed in two pieces, including an upper portion 84 and a lower portion 86 joined by a snaplock connector 88, which facilitates assembly of the unit prior to use, as described in more detail below. A lower seal 90 and an upper seal 92 are positioned in slots on the mixing rod which are aligned with the passages 82 and 80, respectively, when the mixing rod 80 is drawn upwardly, as shown in FIG. 8. A mixing disk 94 is attached at the lower end of the mixing rod 80 and includes both holes 96 and mixing nubs 98 to facilitate combining the liquid L and power P, as will be described below in more detail. A lower connector 100 is formed at the bottom of the syringe body 52 and is covered by a cap 102 or otherwise plugged prior to use of the device.

The mixing syringe 50 may be used as follows. The lower portion 86 of the mixing rod 80 including the mixing disk 94 is placed through the bottom passage 82 of the plunger 54 so that sliding seal (usually an O-ring) 104 forms a hermetic seal in the passage. With the open end of the plunger 54 pointed upwardly, the liquid L to be mixed is poured into the hollow interior of the plunger 50. While continuing to hold the plunger in an upright position, the sealing cylinder 70 is inserted into the interior of the plunger and locked in place by locking element 106, typically a resilient tab on the sealing cylinder which mates in a corresponding slot in the wall of the plunger. The upper portion 84 of the mixing rod 80 is then inserted into the interior of the sealing cylinder 70 and snapped into place onto the lower portion 86. The sealed volume 78 may then be purged of excess air pressure by momentarily disengaging the sliding seal 72 to equalize pressure between the sealed volume 78 and the atmosphere. Alternatively, a one-way air purging valve may also be used. The cap 102 or other plug is then placed over the luer fitting 100 if it is not already in place. The powder P may then be introduced into the interior of the syringe body 52 so that it collects at its lower end, as shown in FIG. 8. The plunger 56 may then be screwed into place, leaving the mixing disk 94 located above the powder P in the mixing volume 66. Excess air pressure in the chamber 66 may be relieved by turning the mixing syringe 50 up-side-down and momentarily opening the cap 102 or other plug to release excess air.

Mixing the liquid L and powder P is performed by first pushing the mixing rod 80 down so that an annular depression 110 in the lower portion 86 becomes aligned with the passage 82 in the lower surface of the plunger 54. The annular depression 110 leaves a gap through which the liquid is released by gravity into the mixing volume 66 where it combines with the powder P. The mixing rod may then be axially reciprocated and/or rotated about its axis within the mixing volume 66 to mix together the liquid and powder until a desired consistency is reached.

After mixing together of the liquid L and powder P is completed, the mixing rod 80 may be drawn upwardly to return to the position illustrated in FIG. 8. In that position, the volume 66 is sealed from the remainder of the syringe by sliding seals 60 and 104. Air can again be removed from volume 66 by turning the syringe upwardly, remove the cap 102 or other luer plug, and advance the plunger 54, by rotating the plunger, until the mixture reaches the tip of the luer fitting 100. The luer may be connected to any instrument of choice, or may be used to directly apply the mixed material to a target site of interest. Material is delivered by rotating the plunger, achieving precise and controllable delivery.

What is claimed is:

1. A mixing syringe comprising:
   a syringe barrel having a hollow interior and an outlet nozzle at a lower end;
   a plunger having a hollow interior reciprocatably disposed in the hollow interior of the syringe barrel;
   a mixing rod reciprocatably disposed in the hollow interior of the syringe barrel and having a mixing element at its lower end which is adapted to mix material in the hollow interior of the syringe barrel upon reciprocation of the mixing rod, wherein the mixing element has openings to enhance mixing;
   said plunger and mixing rod having a first relative position wherein the hollow interiors of the syringe barrel and of the plunger are sealed from each other and a second relative position wherein the hollow interiors are in fluid communication.

2. A mixing syringe as in claim 1, further comprising a frangible seal over the nozzle and a mandrel coupled to the mixing rod or plunger for blocking the seal.

3. A mixing syringe as in claim 1, wherein the mixing element comprises a mixing disk.

4. A mixing syringe as in claim 1, wherein the mixing rod is coaxially disposed through a passage in a bottom well of the plunger.

5. A mixing syringe as in claim 4, wherein the mixing rod seals against the passage in the first relative position but not in the second relative position.

6. A mixing syringe as in claim 1, further comprising a sealing cylinder disposed in the hollow interior of the plunger.

7. A mixing syringe as in claim 6, wherein the mixing rod is disposed through coaxially aligned passages on the plunger and the sealing cylinder.

8. A mixing syringe as in claim 7, further comprising sliding seals on the mixing rod which are positioned to seal against the passages on the plunger and sealing cylinder when in the first relative position but do not seal when in the second relative position.

9. Apparatus for production of mixtures of two components with a container for one component and a container for the other component, and with devices for combining the two components in a mixing space, and devices for extrusion of the finished mixture, characterized by the fact that the powdered component 4 is situated in the lower part of the inner space 21 of the outer hollow cylinder 1, which is closed on its lower end with a bottom 10 that carries a nozzle 2 that is sealed relative to inner space 21 by means of a closure membrane 3, whereas the upper part of the inner space 21 is closed by the lower wall 6 of the inner hollow cylinder 5, in which a sliding seal 8 is present for the required sealing, and that the liquid component 9 is situated in the inner space 18 of the inner hollow cylinder 5, which is disposed to reciprocate in the outer hollow cylinder 1 and is closed on its lower end by the lower wall 6, whereas its upper end is closed by the upper wall 11, and that the lower wall 6, as well as the upper wall 11, each have an opening with the sealing lip 7 and 12 that are closed by those parts of the mixing rod 15 that have the larger diameter 17, and that on the lower part of the mixing rod 15 a torus 20, a section with smaller diameter 19, a mixing disk 22, as well as a mandrel 24 are present.

10. Apparatus according to claim 9, characterized by the fact that a plastic enclosure is present, in which the apparatus according to the invention is sealed airtight.

11. Apparatus according to any of claim 9 or 10, characterized by the fact that the outer hollow cylinder 1 has an annular flange 14, the inner hollow cylinder 5 has an annular flange 13 and the mixing rod 15 has a flange plate 16.

12. Apparatus according to any of claim 9, characterized by the fact that openings 23 are present on the mixing disk 22.

13. Apparatus according to any of claim 9, characterized by the fact that a mandrel 24 is present on the lower end of the mixing rod 15.

14. Apparatus according to any of claim 9, characterized by the fact that an inside thread 29 is present on the inside of the outer hollow cylinder 1 in the upper region, whereas an outside thread 28 is present on the outside of the inner hollow cylinder 5.

15. Apparatus according to any of claim 9, characterized by the fact that knurling 30 is present on the annular flanges 13 and 14.

16. Apparatus according to any of claim 9, characterized by the fact that an annular groove (37) that accommodates the sliding seal 8 is situated on the inner periphery of outer hollow cylinder 1.

17. Apparatus according to any of claim 9, characterized by the fact that an operating part 31 is present on the annular flange 14 of the outer hollow cylinder 1 that consists of a connection part 32, a spring element 33, an operating element 34, as well as a detent 35, and that toothing 36 is present on the outer periphery of the inner hollow cylinder 5.

* * * * *